(12) United States Patent
Godinot et al.

(10) Patent No.: US 6,978,243 B2
(45) Date of Patent: Dec. 20, 2005

(54) METHOD FOR THE ANALYSIS OF SENSORY PERCEPTION

(75) Inventors: Nicolas Marie Pierre Godinot, Matawan, NJ (US); Krystyna Malgorzata Rankin, Ridgewood, NJ (US); Carol M. Christensen, Metuchen, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 656 days.

(21) Appl. No.: 09/862,946

(22) Filed: May 22, 2001

(65) Prior Publication Data

US 2002/0177756 A1   Nov. 28, 2002

(51) Int. Cl.[7] ............................................. G06F 17/60
(52) U.S. Cl. ....................................................... 705/1
(58) Field of Search ............................................ 705/1

(56) References Cited

U.S. PATENT DOCUMENTS

| | | | | |
|---|---|---|---|---|
| 4,878,384 A | * | 11/1989 | Bruhn | 73/379.01 |
| 4,953,968 A | * | 9/1990 | Sherwin et al. | 351/211 |
| 5,267,146 A | * | 11/1993 | Shimizu et al. | 703/1 |
| 5,507,291 A | * | 4/1996 | Stirbl et al. | 600/407 |
| 5,542,849 A | * | 8/1996 | Douglass | 434/236 |
| 5,941,833 A | * | 8/1999 | Lipman | 600/555 |
| 6,058,367 A | * | 5/2000 | Sutcliffe et al. | 705/1 |
| 6,353,810 B1 | * | 3/2002 | Petrushin | 704/236 |
| 2002/0042912 A1 | * | 4/2002 | Iijima et al. | 725/14 |

FOREIGN PATENT DOCUMENTS

| | | | | |
|---|---|---|---|---|
| DE | 3518489 A1 | * | 12/1986 | A61B 5/16 |
| JP | 03294914 A | * | 12/1991 | G06C 3/00 |
| JP | 07309084 A | * | 11/1995 | B42D 15/00 |

OTHER PUBLICATIONS

Kleiner, Kurt, "New-Fangled R&D Key to Spicey Success," Baltimore Business Journal, v6, n13, s1, p1, Sep. 5, 1988.*
Behan, John, "Sensory analysis in the fragrance industry." Cosmetics and Toiletries, v105, n6, p35(5), Jun. 1990.*
Darrington, Hugh, "Extra sensory perception." Food Manufacture, v65, n8, p51(2), Oct. 1990.*
www.rssl.com, Screen Print, Apr. 10, 2001.*
Herrinton, Kay, "Sensory evaluation—or getting the tast right." Dairy Industries International, v56, n3, p31(2), Mar. 1991.*
Sanderson, Tracey, "Learning from Bitter Experience: A Case Study of the Benefits of Sensory Evaluation," Specialty Chemicals, p409, Dec. 1992.*
"It's all in the smell." Food Engineering International, v20, n1, p38(1), Feb. 1995.*
Cowart, B.J., "The Addition of $CO_2$ to Traditional Taste Solutions Alters Taste Quality", Chem. Senses 23:397-402, 1998.

* cited by examiner

Primary Examiner—John G. Weiss
Assistant Examiner—Jonathan Ouellette
(74) Attorney, Agent, or Firm—Joseph F. Leightner; Alexander Migirov

(57) ABSTRACT

A method is provided in which the sensory perceptions of the subject are represented in a visual manner, the method provides for a computation of the attributes to automatically total the perceptions tested such that the results to equal 100%. In a preferred embodiment the results are provided as a pie chart or a bar chart with each of the attributes tested provided in a different color to accentuate the relative proportions of the attributes.

12 Claims, 3 Drawing Sheets

METHOD FOR THE ANALYSIS OF SENSORY PERCEPTION

FIELD OF THE INVENTION

The present invention is directed to a method for collection and display of the relative contribution of individual sensory attributes in the total perception of a stimulus.

BACKGROUND OF THE INVENTION

Respondents are frequently surveyed about their perceptions of a whole host of consumer products that include food, oral care, fragrances as well as other product categories that may also involve visual and/or auditory elements. A typical survey includes questions that aim to estimate the perceived intensity of a number of attributes that describe a given product. In the food category, the list could include such attributes as sweet, sour, salty, bitter and/or other. However, intensity ratings are not the most sensitive way of capturing more subtle but real differences between products that vary along only one, but very important dimension, or groups of people who may vary in their sensitivity to a particular stimulus. See, for example, Cowart, Beverly J., *The Addition of $CO_2$ to Traditional Taste Solutions Alters Taste Quality*, Chem Senses 23: 397–402, 1998. In this study the subjects were required to (a) rate the intensity of different taste qualities of a beverage on an intensity scale, and (b) rate the relative contribution of each of those qualities where the total perception had to add up to 100%. The latter method was able to show clear difference in the perception of the various beverages while the first method failed to pick out those differences.

However, having to rate the relative proportions of several attributes at the same time and making sure that they add up to 100% may be difficult and confusing to an average consumer. The resulting data may be inaccurate. This method would be an improvement if we could eliminate the need to perform the mathematical computations while simultaneously providing a visible indication of the relative contribution of each attribute being surveyed.

SUMMARY OF THE INVENTION

The present invention provides a method that allows the subject to represent his/her perception of a complex sensory stimulus as a visual image. Using this method, the subject rates the relative contribution of each quality of that sensation with the objective that the sum of the individual qualities must equal 100% of the total perception. As the subject has a visual representation of his/her ratings, there is no need for any calculation on the subject's part. Thus, the present invention comprises a method for visually presenting the attributes of a sensory perception comprising:
  (a) providing a subject;
  (b) providing the subject with a sensory perception scale on a computing device containing a plurality of attributes, said sensory perception scale having variable positions;
  (c) providing the subject with a test sample and requesting said subject to sample the test sample;
  (d) asking the subject to rate the attributes of the samples by manipulating the positions of the perception scale; and
  (e) providing the position of the variable position scale to a computing means, said computing means providing a visual interpretation on a screen of the attributes of the sample.

The present invention can be used to measure the relative contribution of various qualities or attributes to a total perception in all the sensory modalities: taste, smell, color, touch, hearing, as well as perception of emotion. The method can be used to measure two or more attributes perceived and the relative contribution of each. Ideally the variable position scale and the visual interpretation of the results are both done on a computer screen, preferably on the same screen so that as the different attributes are manipulated, the results are visible to the subject on the same computer screen.

DETAILED DESCRIPTION OF THE INVENTION

Figure 1:
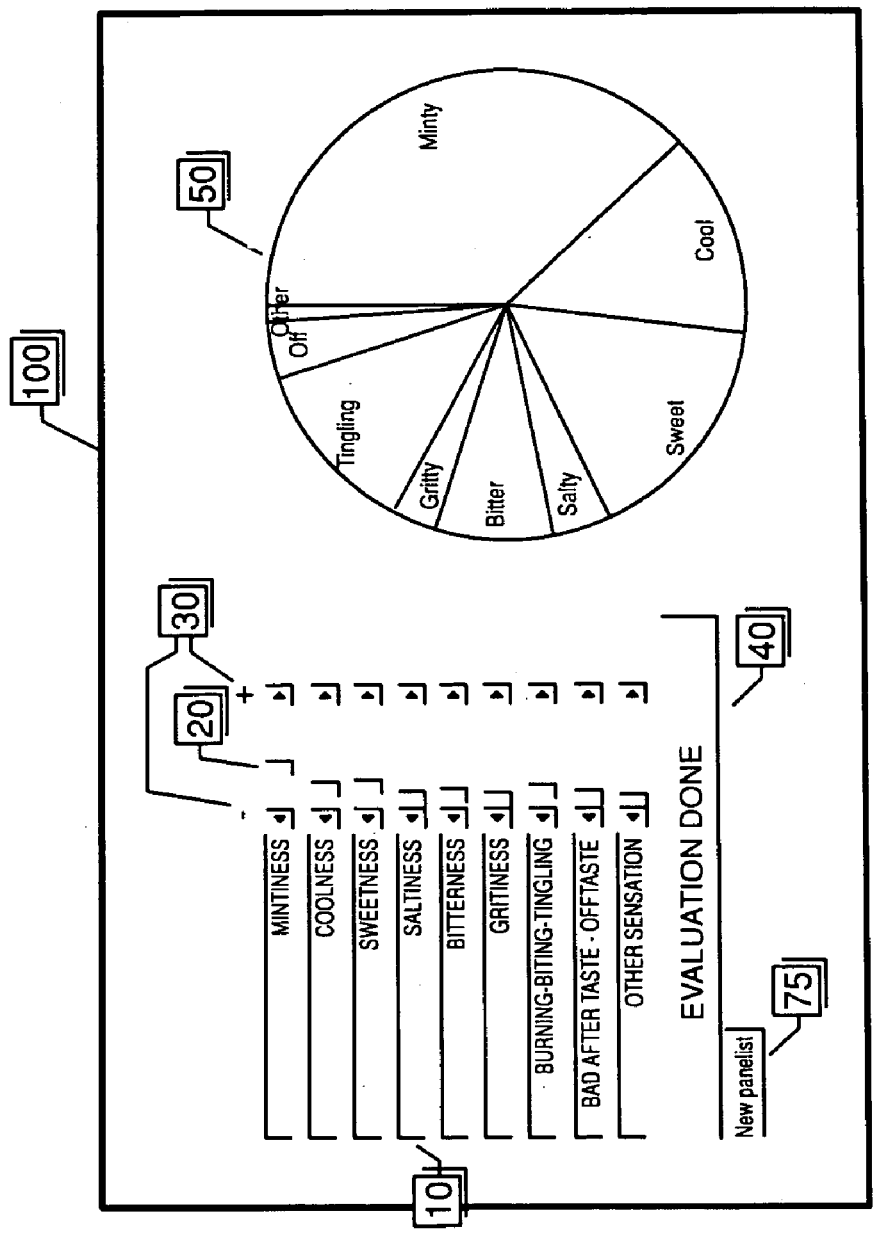
FIG. 1 depicts the plurality of attributes and the resulting visual depiction of the results as a pie chart.

The method of the present invention can be used to measure the relative contribution of two or more qualities or attributes simultaneously, preferably from about 4 to about 6 attributes per given stimulus but more attributes can be measured.

The present invention allows the number of attributes or qualities to be varied across studies so as to specifically tailor the study to the stimuli to be tested.

When the present invention is being used the number of attributes that are required to describe a stimulus being tested is easily adjusted (increased or decreased). For example, an oral stimulus (e.g., oral car product) may contain a flavor where only two to four attributes are relevant to measure, whereas a more complex fragrance product, such as a perfume, may need 10 to 12 attributes.

Within the taste modality (including the basic tastes, as well as flavor, texture, temperature, other sensations experienced in the mouth), attributes that can be tested include but are not limited to: sweetness, saltiness, bitterness, sourness, mintiness, coolness, grittiness, burning, biting, tingling, bad after taste, metallic and the like.

Within the olfactory modality (smell) attributes that can be tested include but are not limited to citrus, floral, fruity, woody, spicy, leathery, herbaceous, musk, amber, oriental and the like.

Within the visual modality attributes that can be tested include but are not limited to: color (saturation, hue, brightness), shape (angular, roundness), length, and the like.

Within the tactile modality (touch) attributes that can be tested include but are not limited to: smoothness/roughness, thermal, chemosensory, pain, and the like.

Within the auditory modality (hearing), attributes that can be tested include but are not limited to: sound quality, pitch, timbre, and the like.

Within perception of emotional states, attributes that can be tested include but are not limited to: moods or other internal states such as happy, sad, angry, irritated, relaxed, excited, stressed, sensual and the like.

When using the method of the present invention the predetermined attributes are presented to a subject. The subject is then asked to sample the test stimulus and evaluate the relative contribution of each attribute to the total perception. The subject is then instructed to represent his/her perception of that stimulus visually on a computer screen (or paper). If the subject uses the computer he/she directs the cursor on the screen onto the controls and manipulates them to provide an image of the various attributes of the sample. The control for each of the attributes can be any suitable mechanism, such as a dial that is rotated clockwise or counter-clockwise. In a preferred embodiment a slide device is employed to increase or decrease the relative value of the attribute.

After the control for each of the attributes has been manipulated, a visual image is generated which demonstrates the relative proportions of the attributes. The control for each of the attributes can be numbered such as from 1 to 10, or in a preferred embodiment labeled simply with a (+) for increasing or (−) for decreasing the proportion of contribution of that attribute. The different attributes can be displayed as a bar chart or in a preferred embodiment as a pie chart, in a preferred embodiment the attributes are displayed in different colors or shading or patterns to distinguish the level of the attribute.

The graphical representation and computation of the relative values of the attributes can be provided through the application of commonly available software such as MICROSOFT® Excel. Using the visual basic option for application optionally a pie chart can be used to visually create an impression of the attributes being tested. The pie represents total perception of the stimulus and the segments of the pie represent the individual attributes or qualities. Another graphical representation of the relative values of the attributes is a bar chart.

The present invention has several advantages over the sensory testing procedures previously employed. To many subjects sensory perception is difficult to quantify numerically. It is much easier to employ visual means to represent perception through use of colors and familiar shapes or graphs. Another advantage is the elimination of the need to perform arithmetic computations to determine whether the attributes add up to 100 percent. Having the software perform the computations ensure that the attributes add up to 100% while freeing the subjects from tiresome arithmetic computations.

Referring to FIG. 1, a simulated computer screen 100 is depicted and 9 different attributes 10 for flavor are presented: 1) mintiness, 2) coolness, 3) sweetness, 4) saltiness, 5) bitterness, 6) grittiness, 7) burning-biting tingling; 8) bad after taste-off-taste and 9) other sensation. The perception scale 20 is provided for each of the attributes, with a (−) and (+) guides 30 provided to indicate relative proportion of the attributes. The subject is asked to manipulate the relative position of the attributes after evaluating the stimulus. The computing means then produces the pie chart 50 with the relative size of each value present, preferably with the attribute also appearing in the proximity of the pie chart as depicted in FIG. 1. In a preferred embodiment, an EVALUATION DONE icon 40 is provided to initiate when the computations should be done and the visual interpretation of the results generated. An optional NEW PANELIST icon 75 (subject) is provided to allow a new subject to begin the test.

Figure 2:
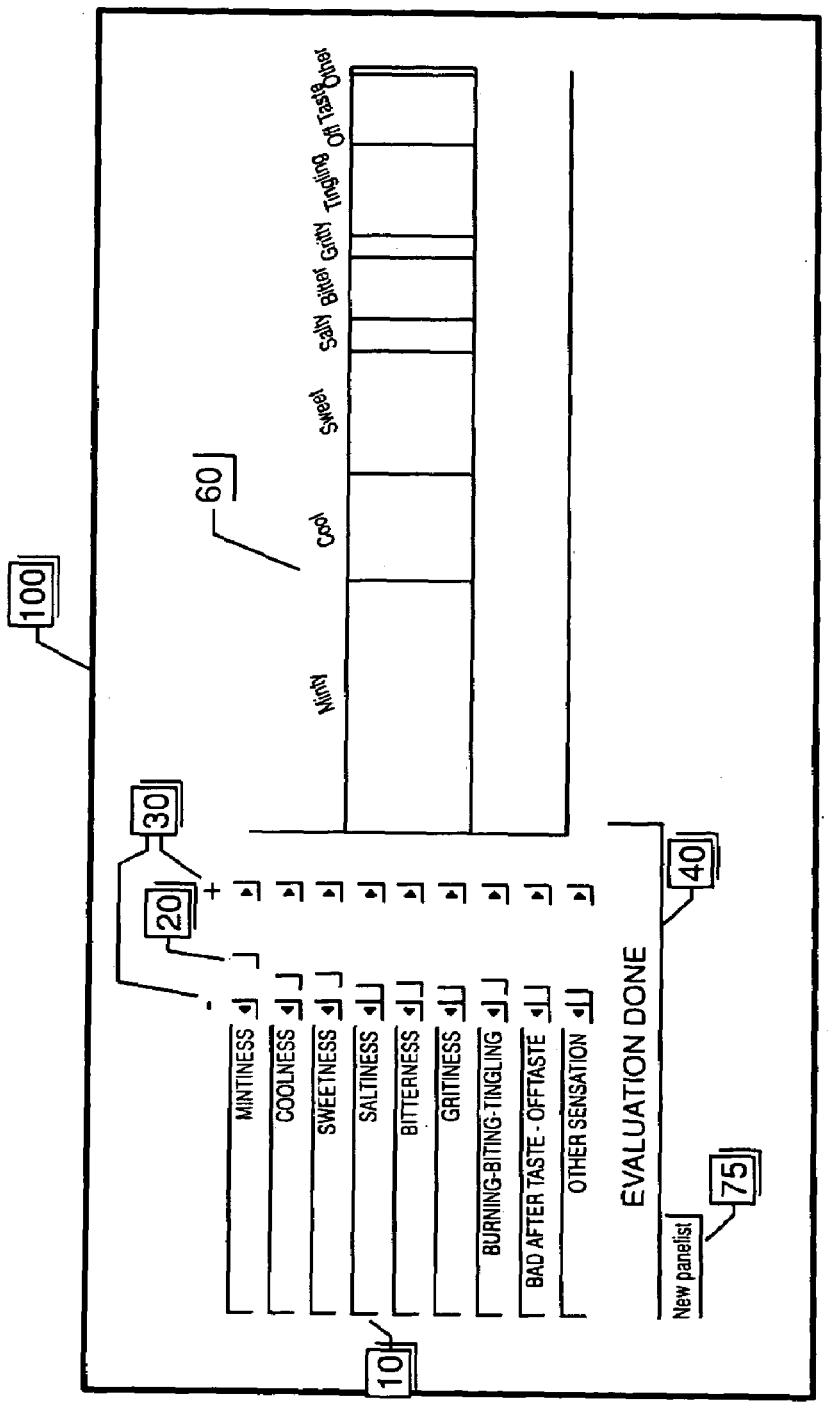
FIG. 2 depicts the plurality of attributes and the resulting visual depiction of the results as a single bar chart.

Referring to FIG. 2, a simulated computer screen 100 is depicted and 9 different attributes 10 for flavor are presented: 1) mintiness, 2) coolness, 3) sweetness, 4) saltiness, 5) bitterness, 6) grittiness, 7) burning-biting tingling; 8) bad after taste- offtaste and 9) other sensation. The perception scale 20 is provided for each of the attributes, with a (−) and (+) guides 30 provided to indicate relative proportion of attributes. The subject is asked to manipulate the relative position of the attributes after sampling the food. The computing means then produces the bar chart 60 with the relative size of each value present, preferably with the attribute also appearing in the proximity of the pie chart as depicted in FIG. 2. In a preferred embodiment, an EVALUATION DONE icon 40 is provided to initiate when the computations should be done and the visual interpretation of the results generated. An optional new panelist icon 75 (subject) is provided to allow a new subject to begin the test.

As used herein, computer is understood to mean any device that is capable of making mathematical computations such as arithmetic calculations and then displaying the results on a display device. Preferably the computer has a display screen which has the capability to display the results of the computations, preferably as a pie chart or a bar chart. Display devices include but are not limited to liquid crystal displays (LCDs); cathode ray tubes (CRTs) and personal digital assistants (PDAs).

The present invention has several advantages over sampling techniques used previously. Since the computing device is used to perform the mathematical computations, mathematical errors are avoided. In addition since most people are not analytically oriented, the visual display of the results has been found to be very helpful in comparing the relative proportions of the attributes. Also the use of the computer allows the subjects to quickly screen various samples and makes the sampling process fun to the subjects.

The following example is meant to exemplify the present invention without limiting the scope of the invention, which is defined by the claims. Unless noted to the contrary, all numbers are understood to be percent of the total sensory perception perceived by the subjects.

EXAMPLE 1

Thirty-four women panelists participated in a test to evaluate a commercially marketed toothpaste that contained baking soda and peroxide. The women were classified into 2 groups based on genetic variation of taste phenotype. Eighteen panelists were classified into group 1 (40-±3 years old), and 16 into group 2 (40±4 years old).

During the test, the panelists brushed their teeth with the product, 15 seconds on one side of the mouth, 15 seconds on the other side. Prior to rinsing the panelists were asked to rate their liking of the product (9 point hedonic scale), its overall intensity (9 point intensity scale) and the relative contribution of 8 attributes to the overall flavor ('minty', 'coolness', 'sweetness', 'saltiness', 'bitterness', 'griminess', 'burning-biting-tingling', 'bad after-taste/off-taste') using the method described in the above specification. The panelists made the same evaluation just after rinsing (time 0), at 2 minutes, 4 minutes, 8 minutes and 15 minutes after rinsing. At the end of the 15-minute evaluation, they again evaluated their overall liking of the product.

Figure 3:
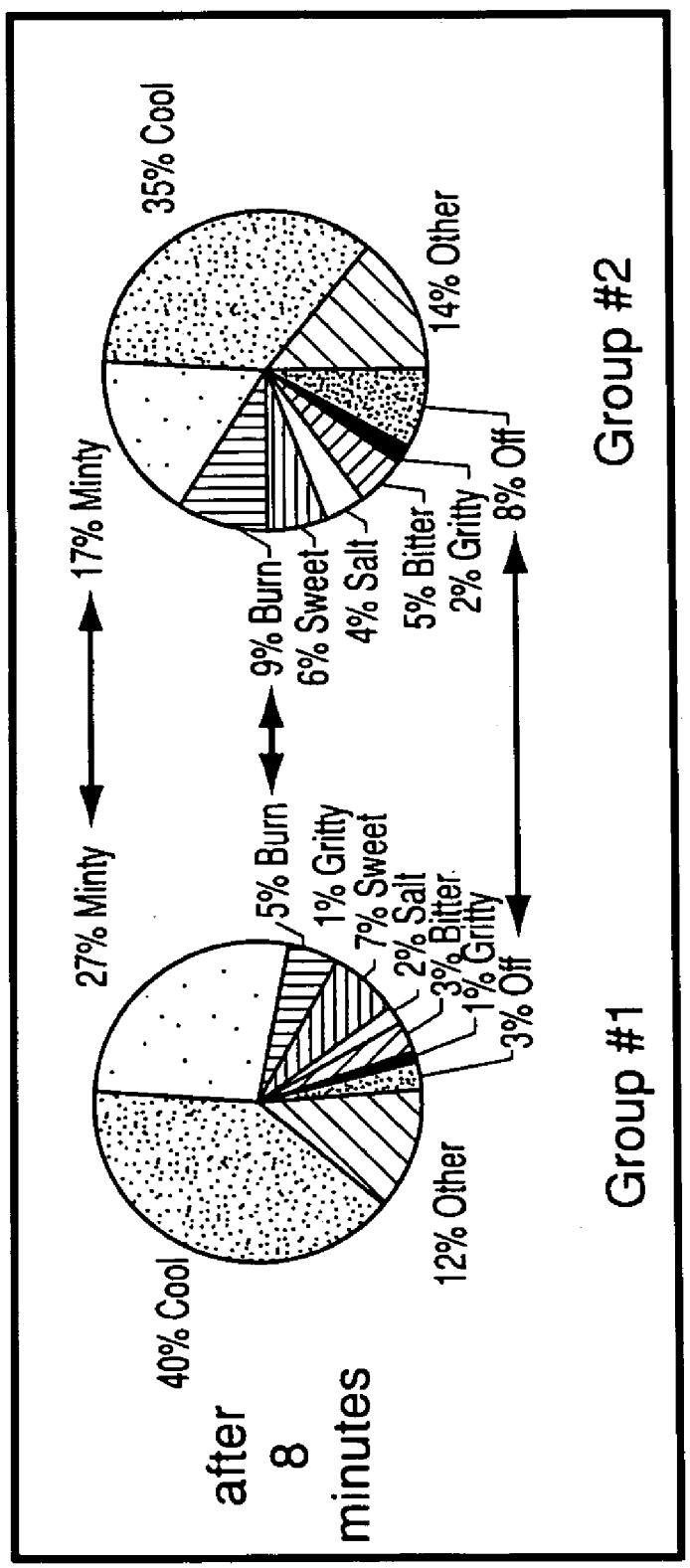
FIG. 3 depicts the results of testing of Example 1 set forth herein below.

The chart set forth in FIG. 3 depicts the average proportion of the 9 attributes tested for the 2 groups of women 8 minutes after rinsing their mouth with water. Using the attribute value testing set forth above and appropriate statistical methods, it was determined that the women in group 2 perceived the flavor of the tested product differently than women of group 1. The women of group 2 reported a higher proportion of off-flavor, more burning, and less minuteness than women in-group 1. These findings were correlated with the panelists' hedonic ratings set forth in FIG. 3.

We claim:

1. A method for visually presenting the taste attributes of a sample comprising:

(a) providing a subject;

(b) providing the subject with a sensory perception scale for taste on a computing device containing a plurality of attributes selected from the group consisting of sweetness, saltiness, bitterness, sourness, mintiness, coolness, grittiness, burning, biting, tingling, bad after taste, and metallic; said sensory perception scale having variable positions;

(c) providing the subject with a test sample and requesting said subject to sample the test sample;

(d) asking the subject to rate from 4 to 6 attributes of the samples selected from the group consisting of from sweetness, saltiness, bitterness, sourness, mintiness, coolness, grittiness, burning, biting, tingling, bad after taste, and metallic; by manipulating the positions of the perception scale; and (e) providing the position of the variable position scale to a computing means, said computing means providing a simultaneous visual interpretation on a screen of the attributes of the sample.

2. The method of claim 1 wherein the visual interpretation of the attributes of the sample is provided as a pie chart.

3. The method of claim 1 wherein the visual interpretation of the attributes of the sample is provided as a single bar chart.

4. The method of claim 2 wherein the relative value of each attribute is provided by a unique color.

5. The method of claim 3 wherein the relative value of each attribute is provided by a unique color.

6. The method of claim 1 wherein the visual interpretation of the attributes of the sample is generated without having the subject perform any mathematical computation.

7. A method for visually presenting the olfactory attributes of a sample comprising:

(a) providing a subject;

(b) providing the subject with a sensory perception scale for olfaction on a computing device containing a plurality of attributes selected from the group consisting of citrus, floral fruity, woody spicy leathery, herbaceous, musk, amber and oriental; said sensory perception scale having variable positions;

(c) providing the subject with a test sample and requesting said subject to sample the test sample;

(d) asking the subject to rate from 4 to 6 attributes of the sample's attributes selected from the group consisting of citrus, floral fruity, woody spicy leathery, herbaceous, musk, amber and oriental by manipulating the positions of the perception scale; and (e) providing the position of the variable position scale to a computing means, said computing means providing a simultaneous visual interpretation on a screen of the attributes of the sample.

8. The method of claim 7 wherein the visual interpretation of the attributes of the sample is provided as a pie chart.

9. The method of claim 7 wherein the visual interpretation of the attributes of the sample is provided as a single bar chart.

10. The method of claim 8 wherein the relative value of each attribute is provided by a unique color.

11. The method of claim 9 wherein the relative value of each attribute is provided by a unique color.

12. The method of claim 7 wherein the visual interpretation of the attributes of the sample is generated without having the subject perform any mathematical computation.

* * * * *